United States Patent [19]
Burgett et al.

[11] Patent Number: 6,162,617
[45] Date of Patent: Dec. 19, 2000

[54] STREPTOCOCCUS PNEUMONIAE GENE SEQUENCE DNAG

[75] Inventors: Stanley Gene Burgett; Jo Ann Hoskins, both of Indianapolis, Ind.; Stanley Richard Jaskunas, Jr., Natick, Mass.; Robert Brown Peery, Brownsburg, Ind.; Paul Robert Rosteck, Jr.; Genshi Zhao, both of Indianapolis, Ind.

[73] Assignee: Eli Lilly and Company, Indianapolis, Ind.

[21] Appl. No.: 08/987,151

[22] Filed: Dec. 8, 1997

Related U.S. Application Data

[60] Provisional application No. 60/036,281, Dec. 13, 1996.
[51] Int. Cl.[7] .......................... C12P 21/06; C12P 21/04; C12N 1/00; C12N 1/12
[52] U.S. Cl. ...................... 435/69.1; 435/69.7; 435/71.1; 435/41; 435/243.1; 435/252.1; 435/252.3; 435/253.4; 536/23.1; 536/23.2; 536/23.4
[58] Field of Search ................................ 536/23.1, 23.2, 536/23.4; 435/320.1, 41, 69.1, 69.7, 71.1, 743, 252.1, 253.4

[56] References Cited

U.S. PATENT DOCUMENTS 4,960,707 10/1990 Lacks ....................................... 435/320

OTHER PUBLICATIONS

Grebe et al. J Bacteriol 179(10):3342–3349, May 1997.
Herzog et al DNA and Cell Biol 12 (6), 465–741, 1993.
Jazin et al. Reg Pep 47:247–258, 1993.

Killu Tougu and Kenneth J. Marians. "The Extreme C Terminus of Primase Is Required for Interaction with DnaB at the Replication Fork." *The Journal of Biological Chemistry* 271(35):21391–21397 (Aug. 30, 1996).

Sungsub Kim, et al. "τCouples the Leading– and Lagging– Strand Polymerases at the *Escherichia coli* DNA Replication Fork." *The Journal of Biological Chemistry* 271(35):21406–21412 (Aug. 30, 1996).

Markus Grompe, et al. "Mutati0ons in the *Escherichia coli* dnaG Gene Suggest Coupling between DNA Replication and Chromosome Partitioning." *Journal of Bacteriology* 173(3):1268–1278 (Feb. 1991).

Lee Rowen and Arthur Kornberg. "Primase, the dnaG Protein of *Escherichia coli*: An Enzyme which Starts DNA Chains" *The Journal of Biological Chemistry* 253(3):758–764 (Feb. 10, 1978).

Robert A. Britton, et al. "Characterization of Mutations Affecting the *Escherichia coli* Essential GTPase Era That Suppress Two Temperature–Sensitive dnaG Alleles." *Journal of Bacteriology* 179(14):4575–4582 (Jul. 1997).

*Primary Examiner*—Phuong T. Bui
*Assistant Examiner*—Li Lee
*Attorney, Agent, or Firm*—Charles E. Cohen; Thomas D. Webster

[57] ABSTRACT

The invention provides isolated nucleic acid compounds encoding dnaG of *Streptococcus pneumoniae*. Also provided are vectors and transformed host cells for expressing the encoded protein, and a method for identifying compounds that bind and/or inhibit said protein.

22 Claims, No Drawings

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1785 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: CDS
      (B) LOCATION: 1..1782

(xi) SEQUENCE DESCRIPTION: SEQ ID NO:1:

```
ATG ATA ACC ATG GAG GTA TTG TGT ATG GTT GAC AAA CAA GTC ATT GAA      48
Met Ile Thr Met Glu Val Leu Cys Met Val Asp Lys Gln Val Ile Glu
  1               5                  10                  15

GAA ATC AAA AAC AAT GCC AAC ATT GTG GAA GTC ATA GGA GAT GTG ATT      96
Glu Ile Lys Asn Asn Ala Asn Ile Val Glu Val Ile Gly Asp Val Ile
             20                  25                  30

TCT TTA CAA AAG GCA GGA CGG AAC TAT CTA GGG CTC TGT CCT TTT CAT     144
Ser Leu Gln Lys Ala Gly Arg Asn Tyr Leu Gly Leu Cys Pro Phe His
         35                  40                  45

GGT GAA AAA ACA CCT TCT TTC AGC GTT GTA GAG GAC AAG CAG TTT TAC     192
Gly Glu Lys Thr Pro Ser Phe Ser Val Val Glu Asp Lys Gln Phe Tyr
     50                  55                  60

CAC TGT TTT GGT TGT GGT CGC TCA GGT GAT GTC TTT AAA TTC ATC GAG     240
His Cys Phe Gly Cys Gly Arg Ser Gly Asp Val Phe Lys Phe Ile Glu
 65                  70                  75                  80

GAG TAC CAA GGG GTT ACC TTT ATG GAG GCT GTC CAA ATC TTA GGT CAG     288
Glu Tyr Gln Gly Val Thr Phe Met Glu Ala Val Gln Ile Leu Gly Gln
                 85                  90                  95

CGT GTC GGG ATT GAG GTT GAA AAA CCG CTT TAT AGT GAA CAG AAG CCA     336
Arg Val Gly Ile Glu Val Glu Lys Pro Leu Tyr Ser Glu Gln Lys Pro
            100                 105                 110

GCC TCG CCT CAC CAA GCT CTT TAT GAT ATG CAC GAA GAT GCG GCT AAA     384
Ala Ser Pro His Gln Ala Leu Tyr Asp Met His Glu Asp Ala Ala Lys
        115                 120                 125

TTT TAC CAT GCT ATT CTC ATG ACA ACG ACT ATG GGC GAA GAG GCC AGA     432
Phe Tyr His Ala Ile Leu Met Thr Thr Thr Met Gly Glu Glu Ala Arg
    130                 135                 140

AAT TAC CTT TAT CAG CGG GGT TTG ACA GAT GAA GTG CTT AAA CAT TTT     480
Asn Tyr Leu Tyr Gln Arg Gly Leu Thr Asp Glu Val Leu Lys His Phe
145                 150                 155                 160

TGG ATT GGT TTA GCA CCT CCA GAA CGA AAC TAT CTC TAT CAA CGT TTG     528
Trp Ile Gly Leu Ala Pro Pro Glu Arg Asn Tyr Leu Tyr Gln Arg Leu
                165                 170                 175

TCT GAT CAG TAT CGT GAA GAG GAT TTA CTG GAT TCA GGC TTG TTT TAT     576
Ser Asp Gln Tyr Arg Glu Glu Asp Leu Leu Asp Ser Gly Leu Phe Tyr
            180                 185                 190

CTT TCG GAT GCC AAT CAA TTT GTA GAC ACC TTT CAC AAT CGC ATT ATG     624
Leu Ser Asp Ala Asn Gln Phe Val Asp Thr Phe His Asn Arg Ile Met
        195                 200                 205
```

```
TTT CCC CTG ACA AAT GAC CAA GGA AAG GTC ATT GCC TTC TCA GGT CGT     672
Phe Pro Leu Thr Asn Asp Gln Gly Lys Val Ile Ala Phe Ser Gly Arg
    210                 215                 220

ATC TGG CAA AAA ACG GAT TCA CAA ACT TCT AAG TAT AAA AAC AGC CGA     720
Ile Trp Gln Lys Thr Asp Ser Gln Thr Ser Lys Tyr Lys Asn Ser Arg
225                 230                 235                 240

TCG ACT GTA ATT TTT AAC AAA AGT TAC GAA TTA TAT CAT ATG GAT AGG     768
Ser Thr Val Ile Phe Asn Lys Ser Tyr Glu Leu Tyr His Met Asp Arg
                245                 250                 255

GCA AAA AGA TCT TCT GGA AAA GCT AGT GAG ATT TAC CTG ATG GAA GGA     816
Ala Lys Arg Ser Ser Gly Lys Ala Ser Glu Ile Tyr Leu Met Glu Gly
                260                 265                 270

TTC ATG GAT GTT ATT GCA GCC TAT CGG GCT GGA ATC GAA AAT GCT GTG     864
Phe Met Asp Val Ile Ala Ala Tyr Arg Ala Gly Ile Glu Asn Ala Val
            275                 280                 285

GCG TCG ATG GGA ACG GCC TTG AGT CGA GAG CAT GTT GAG CAT CTG AAA     912
Ala Ser Met Gly Thr Ala Leu Ser Arg Glu His Val Glu His Leu Lys
        290                 295                 300

AGG TTA ACC AAG AAA TTG GTT CTT GTT TAC GAT GGA GAT AAG GCT GGG     960
Arg Leu Thr Lys Lys Leu Val Leu Val Tyr Asp Gly Asp Lys Ala Gly
305                 310                 315                 320

CAA GCC GCG ACA TTG AAA GCA TTG GAT GAA ATT GGT GAT ATG CCT GTG    1008
Gln Ala Ala Thr Leu Lys Ala Leu Asp Glu Ile Gly Asp Met Pro Val
                325                 330                 335

CAA ATC GTC AGC ATG CCT GAT AAC TTG GAT CCT GAT GAA TAT CTA CAA    1056
Gln Ile Val Ser Met Pro Asp Asn Leu Asp Pro Asp Glu Tyr Leu Gln
                340                 345                 350

AAA AAT GGT CCA GAA GAC TTG GCC TAT CTA TTA ACG AAA ACT CGT ATT    1104
Lys Asn Gly Pro Glu Asp Leu Ala Tyr Leu Leu Thr Lys Thr Arg Ile
                355                 360                 365

AGT CCG ATT GAG TTC TAC ATT CAT CAG TAC AAA CCT GAA AAC GGT GAA    1152
Ser Pro Ile Glu Phe Tyr Ile His Gln Tyr Lys Pro Glu Asn Gly Glu
            370                 375                 380

AAT CTG CAG GCT CAG ATT GAG TTT CTT GAA AAA ATA GCT CCC TTG ATT    1200
Asn Leu Gln Ala Gln Ile Glu Phe Leu Glu Lys Ile Ala Pro Leu Ile
385                 390                 395                 400

GTT CAA GAA AAG TCC ATC GCT GCT CAA AAC AGC TAT ATT CAT ATT TTA    1248
Val Gln Glu Lys Ser Ile Ala Ala Gln Asn Ser Tyr Ile His Ile Leu
                405                 410                 415

GCT GAC AGT CTG GCG TCC TTT GAT TAT ACC CAG ATT GAG CAG ATT GTT    1296
Ala Asp Ser Leu Ala Ser Phe Asp Tyr Thr Gln Ile Glu Gln Ile Val
                420                 425                 430

AAT GAG AGT CGT CAG GTG CAA AGG CAG AAT CGC ATG GAA AGA ATT TCC    1344
Asn Glu Ser Arg Gln Val Gln Arg Gln Asn Arg Met Glu Arg Ile Ser
            435                 440                 445

AGA CCG ACG CCA ATC ACC ATG CCT GTC ACC AAG CAG TTA TCG GCT ATT    1392
Arg Pro Thr Pro Ile Thr Met Pro Val Thr Lys Gln Leu Ser Ala Ile
450                 455                 460

ATG AGG GCA GAA GCC CAT CTA CTC TAT CGG ATG ATG GAA TCC CCT CTT    1440
Met Arg Ala Glu Ala His Leu Leu Tyr Arg Met Met Glu Ser Pro Leu
465                 470                 475                 480

GTT TTG AAC GAT TAC CGT TTG CGA GAA GAC TTT GCA TTT GCT ACA CCT    1488
Val Leu Asn Asp Tyr Arg Leu Arg Glu Asp Phe Ala Phe Ala Thr Pro
                485                 490                 495

GAA TTT CAG GTC TTA CAT GAC TTG CTT GGC CAG TAT GGA AAT CTT CCT    1536
Glu Phe Gln Val Leu His Asp Leu Leu Gly Gln Tyr Gly Asn Leu Pro
                500                 505                 510

CCA GAA GTT TTA GCA GAG CAG ACA GAG GAA GTT GAA AGA GCT TGG TAC    1584
Pro Glu Val Leu Ala Glu Gln Thr Glu Glu Val Glu Arg Ala Trp Tyr
```

```
                515                 520                 525
CAA GTT TTA GCT CAG GAT TTG CCT GCT GAG ATA TCG CCG CAG GAA CTT      1632
Gln Val Leu Ala Gln Asp Leu Pro Ala Glu Ile Ser Pro Gln Glu Leu
        530                 535                 540

AGT GAA GTA GAG ATG ACT CGA AAC AAG GCT CTC TTG AAT CAG GAC AAT      1680
Ser Glu Val Glu Met Thr Arg Asn Lys Ala Leu Leu Asn Gln Asp Asn
545                 550                 555                 560

ATG AGA ATC AAA AAG AAG GTG CAG GAA GCT AGC CAT GTA GGA GAT ACA      1728
Met Arg Ile Lys Lys Lys Val Gln Glu Ala Ser His Val Gly Asp Thr
                565                 570                 575

GAT ACA GCC CTA GAA GAA TTG GAA CGT TTA ATT TCC CAA AAG AGA AGA      1776
Asp Thr Ala Leu Glu Glu Leu Glu Arg Leu Ile Ser Gln Lys Arg Arg
        580                 585                 590

ATG GAG TAA                                                           1785
Met Glu
```

(2) INFORMATION FOR SEQ ID NO:2:

(i) SEQUENCE CHARACTERISTICS:
        (A) LENGTH: 594 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ile Thr Met Glu Val Leu Cys Met Val Asp Lys Gln Val Ile Glu
 1               5                  10                  15

Glu Ile Lys Asn Asn Ala Asn Ile Val Glu Val Ile Gly Asp Val Ile
                20                  25                  30

Ser Leu Gln Lys Ala Gly Arg Asn Tyr Leu Gly Leu Cys Pro Phe His
            35                  40                  45

Gly Glu Lys Thr Pro Ser Phe Ser Val Val Glu Asp Lys Gln Phe Tyr
        50                  55                  60

His Cys Phe Gly Cys Gly Arg Ser Gly Asp Val Phe Lys Phe Ile Glu
65                  70                  75                  80

Glu Tyr Gln Gly Val Thr Phe Met Glu Ala Val Gln Ile Leu Gly Gln
                85                  90                  95

Arg Val Gly Ile Glu Val Glu Lys Pro Leu Tyr Ser Glu Gln Lys Pro
            100                 105                 110

Ala Ser Pro His Gln Ala Leu Tyr Asp Met His Glu Asp Ala Ala Lys
        115                 120                 125

Phe Tyr His Ala Ile Leu Met Thr Thr Thr Met Gly Glu Glu Ala Arg
130                 135                 140

Asn Tyr Leu Tyr Gln Arg Gly Leu Thr Asp Glu Val Leu Lys His Phe
145                 150                 155                 160

Trp Ile Gly Leu Ala Pro Pro Glu Arg Asn Tyr Leu Tyr Gln Arg Leu
                165                 170                 175

Ser Asp Gln Tyr Arg Glu Glu Asp Leu Leu Asp Ser Gly Leu Phe Tyr
            180                 185                 190

Leu Ser Asp Ala Asn Gln Phe Val Asp Thr Phe His Asn Arg Ile Met
        195                 200                 205

Phe Pro Leu Thr Asn Asp Gln Gly Lys Val Ile Ala Phe Ser Gly Arg
        210                 215                 220

Ile Trp Gln Lys Thr Asp Ser Gln Thr Ser Lys Tyr Lys Asn Ser Arg
225                 230                 235                 240

Ser Thr Val Ile Phe Asn Lys Ser Tyr Glu Leu Tyr His Met Asp Arg
```

```
                        245                 250                 255
Ala Lys Arg Ser Ser Gly Lys Ala Ser Glu Ile Tyr Leu Met Glu Gly
                260                 265                 270

Phe Met Asp Val Ile Ala Ala Tyr Arg Ala Gly Ile Glu Asn Ala Val
            275                 280                 285

Ala Ser Met Gly Thr Ala Leu Ser Arg Glu His Val Glu His Leu Lys
        290                 295                 300

Arg Leu Thr Lys Lys Leu Val Leu Val Tyr Asp Gly Asp Lys Ala Gly
305                 310                 315                 320

Gln Ala Ala Thr Leu Lys Ala Leu Asp Glu Ile Gly Asp Met Pro Val
                325                 330                 335

Gln Ile Val Ser Met Pro Asp Asn Leu Asp Pro Asp Glu Tyr Leu Gln
            340                 345                 350

Lys Asn Gly Pro Glu Asp Leu Ala Tyr Leu Leu Thr Lys Thr Arg Ile
        355                 360                 365

Ser Pro Ile Glu Phe Tyr Ile His Gln Tyr Lys Pro Glu Asn Gly Glu
    370                 375                 380

Asn Leu Gln Ala Gln Ile Glu Phe Leu Gly Lys Ile Ala Pro Leu Ile
385                 390                 395                 400

Val Gln Glu Lys Ser Ile Ala Ala Gln Asn Ser Tyr Ile His Ile Leu
                405                 410                 415

Ala Asp Ser Leu Ala Ser Phe Asp Tyr Thr Gln Ile Glu Gln Ile Val
            420                 425                 430

Asn Glu Ser Arg Gln Val Gln Arg Gln Asn Arg Met Glu Arg Ile Ser
        435                 440                 445

Arg Pro Thr Pro Ile Thr Met Pro Val Thr Lys Gln Leu Ser Ala Ile
    450                 455                 460

Met Arg Ala Glu Ala His Leu Leu Tyr Arg Met Met Glu Ser Pro Leu
465                 470                 475                 480

Val Leu Asn Asp Tyr Arg Leu Arg Glu Asp Phe Ala Phe Ala Thr Pro
                485                 490                 495

Glu Phe Gln Val Leu His Asp Leu Leu Gly Gln Tyr Gly Asn Leu Pro
            500                 505                 510

Pro Glu Val Leu Ala Glu Gln Thr Glu Glu Val Glu Arg Ala Trp Tyr
        515                 520                 525

Gln Val Leu Ala Gln Asp Leu Pro Ala Glu Ile Ser Pro Gln Glu Leu
    530                 535                 540

Ser Glu Val Glu Met Thr Arg Asn Lys Ala Leu Leu Asn Gln Asp Asn
545                 550                 555                 560

Met Arg Ile Lys Lys Val Gln Glu Ala Ser His Val Gly Asp Thr
                565                 570                 575

Asp Thr Ala Leu Glu Glu Leu Arg Leu Ile Ser Gln Lys Arg Arg
            580                 585                 590

Met Glu (2) INFORMATION FOR SEQ ID NO:3:

(i) SEQUENCE CHARACTERISTICS:
        (A) LENGTH: 1785 base pairs
        (B) TYPE: nucleic acid
        (C) STRANDEDNESS: single
        (D) TOPOLOGY: linear (ii) MOLECULE TYPE: mRNA (iii) HYPOTHETICAL: NO
```

(iv) ANTI-SENSE: NO (xi) SEQUENCE DESCRIPTION: SEQ ID NO:3:

```
AUGAUAACCA UGGAGGUAUU GUGUAUGGUU GACAAACAAG UCAUUGAAGA AAUCAAAAAC      60

AAUGCCAACA UUGUGGAAGU CAUAGGAGAU GUGAUUUCUU UACAAAAGGC AGGACGGAAC     120

UAUCUAGGGC UCUGUCCUUU UCAUGGUGAA AAAACACCUU CUUUCAGCGU UGUAGAGGAC     180

AAGCAGUUUU ACCACUGUUU UGGUUGUGGU CGCUCAGGUG AUGUCUUUAA AUUCAUCGAG     240

GAGUACCAAG GGGUUACCUU UAUGGAGGCU GUCCAAAUCU UAGGUCAGCG UGUCGGGAUU     300

GAGGUUGAAA AACCGCUUUA UAGUGAACAG AAGCCAGCCU CGCCUCACCA AGCUCUUUAU     360

GAUAUGCACG AAGAUGCGGC UAAAUUUUAC CAUGCUAUUC UCAUGACAAC GACUAUGGGC     420

GAAGAGGCCA GAAAUUACCU UUAUCAGCGG GGUUUGACAG AUGAAGUGCU UAAACAUUUU     480

UGGAUUGGUU UAGCACCUCC AGAACGAAAC UAUCUCUAUC AACGUUUGUC UGAUCAGUAU     540

CGUGAAGAGG AUUUACUGGA UUCAGGCCUG UUUUAUCUUU CGGAUGCCAA UCAAUUUGUA     600

GACACCUUUC ACAAUCGCAU UAUGUUUCCC CUGACAAAUG ACCAAGGAAA GGUCAUUGCC     660

UUCUCAGGUC GUAUCUGGCA AAAAACGGAU UCACAAACUU CUAAGUAUAA AAACAGCCGA     720

UCGACUGUAA UUUUUAACAA AAGUUACGAA UUAUAUCAUA UGGAUAGGGC AAAAAGAUCU     780

UCUGGAAAAG CUAGUGAGAU UUACCUGAUG GAAGGAUUCA UGGAUGUUAU UGCAGCCUAU     840

CGGGCUGGAA UCGAAAAUGC UGUGGCGUCG AUGGGAACGG CCUUGAGUCG AGAGCAUGUU     900

GAGCAUCUGA AAAGGUUAAC CAAGAAAUUG GUUCUUGUUU ACGAUGGAGA UAAGGCUGGG     960

CAAGCCGCGA CAUUGAAAGC AUUGGAUGAA AUUGUGAUA UGCCUGUGCA AAUCGUCAGC    1020

AUGCCUGAUA ACUUGGAUCC UGAUGAAUAU CUACAAAAAA AUGGUCCAGA AGACUUGGCC    1080

UAUCUAUUAA CGAAAACUCG UAUUAGUCCG AUUGAGUUCU ACAUUCAUCA GUACAAACCU    1140

GAAAACGGUG AAAAUCUGCA GGCUCAGAUU GAGUUUCUUG AAAAAAUAGC UCCCUUGAUU    1200

GUUCAAGAAA AGUCCAUCGC UGCUCAAAAC AGCAUAUAUUC AUAUUUUAGC UGACAGUCUG    1260

GCGUCCUUUG AUUAUACCCA GAUUGAGCAG AUUGUUAAUG AGAGUCGUCA GGUGCAAAGG    1320

CAGAAUCGCA UGGAAAGAAU UUCCAGACCG ACGCCAAUCA CCAUGCCUGU CACCAAGCAG    1380

UUAUCGGCUA UUAUGAGGGC AGAAGCCCAU CUACUCUAUC GGAUGAUGGA AUCCCCUCUU    1440

GUUUUGAACG AUUACCGUUU GCGAGAAGAC UUUGCAUUUG CUACACCUGA AUUUCAGGUC    1500

UUACAUGACU UGCUUGGCCA GUAUGGAAAU CUUCCUCCAG AAGUUUUAGC AGAGCAGACA    1560

GAGGAAGUUG AAAGAGCUUG GUACCAAGUU UUAGCUCAGG AUUUGCCUGC UGAGAUAUCG    1620

CCGCAGGAAC UUAGUGAAGU AGAGAUGACU CGAAACAAGG CUCUCUUGAA UCAGGACAAU    1680

AUGAAAUCA AAAAGAAGGU GCAGGAAGCU AGCCAUGUAG GAGAUACAGA UACAGCCCUA    1740

GAAGAAUUGG AACGUUUAAU UUCCCAAAAG AGAAGAAUGG AGUAA                  1785
```

(2) INFORMATION FOR SEQ ID NO:4:

(i) SEQUENCE CHARACTERISTICS:
        (A) LENGTH: 1602 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

```
CCTGATTATA CCCAACCTCT TTGCATCAAG TCGGAAAAAT GAGTGAAATG GGTTTCCAGT        60
TTTCCTGAAA TAAGGTATCC TATATAAAGT ACCCTATGAT AACCATGGAG GTATTGTGTA       120
TGGTTCAAAC AAGTCATTGA AGAAATACAA AACAATGCCA ACATTGTGGA AGTCATAGGA       180
GATGTGATAT CTTACAAAAG GCAGGACGGA ACTATCTAGG GCTCTGTCCT TTTCATGGTG       240
AAAAAACACC ATCTTTCAGC GTTGTAGAGA ACAAGCAGTT TTACCACTGT TTTGGTTGTG       300
GTCGCTCAGG TGATGTCTTT AAAATTCATC GAGGAGTACC AAGGGGTTAC CTTTATGGAG       360
GCTGTCCAAA TCTTAGGTCA GCGTGTCGGG ATTGAGGTTG AAAAACCGCT TTATAGTGAA       420
CAGAAGCCAG CCTCGCCTCA CCAAGCTCTT TATGATATGC ACGAAGATGC GGCTAAATTT       480
TACCATGCTA TTCTCATGAC AACGACTATG GGCGAAGAGG CCAGAAATTA CCTTTATCAG       540
CGGGGTTTGA CAGATGAAGT GCTTAAACAT TTTTGGATTG GTTTAGCACC TCCAGAACGA       600
AACTATCTCT ATCAACGTTT GTCTGATCAG TATCGTGAAG AGGATTTACT GGATTCAGGC       660
CTGTTTTATC TTTCGGATGC CAATCAATTT GTAGACACCT TTCACAATCG CATTATGTTT       720
CCCCTGACAA ATGACCAAGG AAAGGTCATT GCCTTCTCAG GTCGTATCTG GCAAAAAACG       780
GATTCACAAA CTTCTAAGTA TAAAAACAGC CGTTCGACTG TAATTTTTAA CAAAAGTTAC       840
GAATTATATC ATATGGATAG GGCAAAAAGA TCTTCTGGAA AAGCTAGTGA GATTTACCTG       900
ATGGAAGGAT TCATGGATGT TATTGCAGCC TATCGGGCTG GAATCGAAAA TGCTGTGGCG       960
TCGATGGGAA CGGCCTTGAG TCGAGAGCAT GTTGAGCATC TGAAAAGGTT AACCAAGAAA      1020
TTGGTTCTTG TTTACGATGG AGATAAGGCT GGGCAAGCCG CGACATTGAA AGCATTGGAT      1080
GAAATTGGTG ATATGCCTGT GCAAATCGTC AGCATGCCTG ATAACTTGGA TCCTGATGAA      1140
TATCTACAAA AAAATGGTCC AGAAGACTTG GCCTATCTAT TAACGAAAAC TCGTATTAGT      1200
CCGATTGAGT TCTACATTCA TCAGTACAAA CCTGAAAACG GTGAAAATCT GCAGGCTCAG      1260
ATTGAGTTTC TTGAAAAAAT AGCTCCCTTG ATTGTTCAAG AAAAGTCCAT CGCTGCTCAA      1320
AACAGCTATA TTCATATTTT AGCTGACAGT CTGGCGTCCT TTGATTATAC CCAGATTGAG      1380
CAGATTGTTA ATGAGAGTCG TCAGGTGCAA AGGCAGAATC GCATGGAAAG AATTTCCAGA      1440
CCGACGCCAA TCACCATGCC TGTCACCAAG CAGTTATCGG CTATTATGAG GGCAGAAGCC      1500
CATCTACTCT ATCGGATGAT GGAATCCCCT CTCGTTTTGA ACGATTACCG TTTGCGAGAA      1560
GACTTTGCAT TTGCTACACC TGAATTTCAG GTCTTACATG AC                        1602
```

STREPTOCOCCUS PNEUMONIAE GENE SEQUENCE DNAG

This application claims the benefit of U.S. Provisional application Ser. No. 60/036,281, filed Dec. 13, 1996.

BACKGROUND OF THE INVENTION

This invention provides isolated DNA sequences, proteins encoded thereby, and methods of using said DNA and protein in a variety of applications.

Widespread antibiotic resistance in common pathogenic bacterial species has justifiably alarmed the medical and research communities. Frequently, resistant organisms are co-resistant to several antibacterial agents. Penicillin resistance in *Streptococcus pneumoniae* has been particularly problematic. This organism causes upper respiratory tract infections. Modification of a penicillin-binding protein (PBP) underlies resistance to penicillin in the majority of cases. Combating resistance to antibiotic agents will require research into the molecular biology of pathogenic organisms. The goal of such research will be to identify new antibacterial agents.

While researchers continue to develop antibiotics effective against a number of microorganisms, *Streptococcus pneumoniae* has been more refractory. In part, this is because *Streptococcus pneumoniae* is highly recombinogenic and readily takes up exogenous DNA from its surroundings. Thus, there is a need for new antibacterial compounds and new targets for antibacterial therapy in *Streptococcus pneumoniae*.

BRIEF SUMMARY OF THE INVENTION

The present invention relates to an isolated gene and encoded protein from *S. pneumoniae*. The invention enables:
(1) preparation of probes and primers for use in hybridizations and PCR amplifications,
(2) production of proteins and RNAs encoded by said gene and related nucleic acids, and
(3) methods to identify compounds that bind and/or inhibit said protein(s).

In one embodiment the present invention relates to an isolated nucleic acid molecule encoding dnaG protein.

In another embodiment, the invention relates to a nucleic acid molecule comprising the nucleotide sequence identified as SEQ ID NO:1, SEQ ID NO:3, or SEQ ID NO:4.

In another embodiment, the present invention relates to a nucleic acid that encodes SEQ ID NO:2.

In another embodiment the present invention relates to an isolated protein molecule, wherein said protein molecule comprises the sequence identified as SEQ ID NO:2.

In yet another embodiment, the present invention relates to a recombinant DNA vector that incorporates the dnaG gene in operable linkage to gene expression sequences enabling the gene to be transcribed and translated in a host cell.

In still another embodiment the present invention relates to host cells that have been transformed or transfected with the cloned dnaG gene such that said gene is expressed in the host cell.

This invention also provides a method of determining whether a nucleic acid sequence of the present invention, or fragment thereof, is present in a sample, comprising contacting the sample, under suitable hybridization conditions, with a nucleic acid probe of the present invention.

In a still further embodiment, the present invention relates to a method for identifying compounds that bind and/or inhibit the dnaG protein.

DETAILED DESCRIPTION OF THE INVENTION

"ORF" (i.e. "open reading frame") designates a region of genomic DNA beginning with a Met or other initiation codon and terminating with a translation stop codon, that potentially encodes a protein product. "Partial ORF" means a portion of an ORF as disclosed herein such that the initiation codon, the stop codon, or both are not disclosed.

"Consensus sequence" refers to an amino acid or nucleotide sequence that may suggest the biological function of a protein, DNA, or RNA molecule. Consensus sequences are identified by comparing proteins, RNAs, and gene homologues from different species.

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature.

"Essential genes" or "essential ORFs" or "essential proteins" refer to genomic information or the protein(s) or RNAs encoded thereby, that when disrupted by knockout mutation, or by other mutation, result in a loss of viability of cells harboring said mutation.

"Non-essential genes" or "non-essential ORFs" or "non-essential proteins" refer to genomic information or the protein(s) or RNAs encoded therefrom which when disrupted by knockout mutation, or other mutation, do not result in a loss of viability of cells harboring said mutation.

"Minimal gene set" refers to a genus comprising about 256 genes conserved among different bacteria such as *M. genitalium* and *H. influenzae*. The minimal gene set may be necessary and sufficient to sustain life. See e.g. A. Mushegian and E. Koonin, "A minimal gene set for cellular life derived by comparison of complete bacterial genomes" Proc. Nat. Acad. Sci. 93, 10268–273 (1996).

"Knockout mutant" or "knockout mutation" as used herein refers to an in vitro engineered disruption of a region of native chromosomal DNA, typically within a protein coding region, such that a foreign piece of DNA is inserted within the native sequence. A knockout mutation occurring in a protein coding region prevents expression of the wild-type protein. This usually leads to loss of the function provided by the protein. A "knockout cassette" refers to a fragment of native chromosomal DNA having cloned therein a foreign piece of DNA that may provide a selectable marker.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refer to the capacity of purine and pyrimidine nucleotides to associate through hydrogen bonding to form double stranded nucleic acid molecules. The following base pairs are related by complementarity: guanine and cytosine; adenine and thymine; and adenine and uracil. As used herein, "complementary" applies to all base pairs comprising two single-stranded nucleic acid molecules. "Partially complementary" means one of two single-stranded nucleic acid molecules is shorter than the other, such that one of the molecules remains partially single-stranded.

"Oligonucleotide" refers to a short nucleotide chain comprising from about 2 to about 25 nucleotides.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which can be used to hybridize with another nucleic acid compound.

The term "hybridization" or "hybridize" as used herein refers to the process by which a single-stranded nucleic acid molecule joins with a complementary strand through nucleotide base pairing.

"Substantially purified" as used herein means a specific isolated nucleic acid or protein, or fragment thereof, in which substantially all contaminants (i.e. substances that differ from said specific molecule) have been separated from said nucleic acid or protein. For example, a protein may, but not necessarily, be "substantially purified" by the IMAC method as described herein.

"Selective hybridization" refers to hybridization under conditions of high stringency. The degree of hybridization between nucleic acid molecules depends upon, for example, the degree of complementarity, the stringency of hybridization, and the length of hybridizing strands.

The term "stringency" relates to nucleic acid hybridization conditions. High stringency conditions disfavor non-homologous base pairing. Low stringency conditions have the opposite effect. Stringency may be altered, for example, by changes in temperature and salt concentration. Typical high stringency conditions comprise hybridizing at 50° C. to 65° C. in 5×SSPE and 50% formamide, and washing at 50° C. to 65° C. in 0.5×SSPE; typical low stringency conditions comprise hybridizing at 35° C. to 37° C. in 5×SSPE and 40% to 45% formamide and washing at 42° C. in 1×–2×SSPE.

"SSPE" denotes a hybridization and wash solution comprising sodium chloride, sodium phosphate, and EDTA, at pH 7.4. A 20× solution of SSPE is made by dissolving 174 g of NaCl, 27.6 g of $NaH_2PO_4.H_2O$, and 7.4 g of EDTA in 800 ml of $H_2O$. The pH is adjusted with NaOH and the volume brought to 1 liter.

"SSC" denotes a hybridization and wash solution comprising sodium chloride and sodium citrate at pH 7. A 20× solution of SSC is made by dissolving 175 g of NaCl and 88 g of sodium citrate in 800 ml of $H_2O$. The volume is brought to 1 liter after adjusting the pH with 10N NaOH.

DETAILED DESCRIPTION OF THE INVENTION

The dnaG gene disclosed herein (SEQ ID NO:1) and related nucleic acids (for example, SEQ ID NO:3 and SEQ ID NO:4) encode a DNA primase that is a member of the minimal gene set described for bacterial cells.

The proteins categorized as "minimal gene set" counterparts are homologous to a set of highly conserved proteins found in other bacteria. The minimal gene set proteins are thought to be essential for viability and are useful targets for the development of new antibacterial compounds.

In one embodiment, the proteins of this invention are purified, and used in a screen to identify compounds that bind and/or inhibit the activity of said proteins. A variety of suitable screens are contemplated for this purpose. For example, the protein(s) can be labeled by known techniques, such as radiolabeling or fluorescent tagging, or by labeling with biotin/avidin. Thereafter, binding of a test compound to a labeled protein can be determined by any suitable means, well known to the skilled artisan.

Skilled artisans will recognize that the DNA molecules of this invention, or fragments thereof, can be generated by general cloning methods. PCR amplification using oligonucleotide primers targeted to any suitable region of SEQ ID NO:1 is preferred. Methods for PCR amplification are widely known in the art. See e.g. *PCR Protocols: A Guide to Method and Application,* Ed. M. Innis et al., Academic Press (1990) or U.S. Pat. No. 4,889,818, which hereby is incorporated by reference. A PCR comprises DNA, suitable enzymes, primers, and buffers, and is conveniently carried out in a DNA Thermal Cycler (Perkin Elmer Cetus, Norwalk, Conn.). A positive PCR result is determined by, for example, detecting an appropriately-sized DNA fragment following agarose gel electrophoresis.

The DNAs of the present invention may also be produced using synthetic methods well known in the art. (See, e.g., E. L. Brown, R. Belagaje, M. J. Ryan, and H. G. Khorana, *Methods in Enzymology,* 68:109–151 (1979)). An apparatus such as the Applied Biosystems Model 380A or 380B DNA synthesizers (Applied Biosystems, Inc., 850 Lincoln Center Drive, Foster City, Calif. 94404) may be used to synthesize DNA. Synthetic methods rely upon phosphotriester chemistry [See, e.g., M. J. Gait, ed., *Oligonucleotide Synthesis, A Practical Approach,* (1984)], or phosphoramidite chemistry.

Protein Production Methods

The present invention relates further to substantially purified proteins encoded by the gene disclosed herein.

Skilled artisans will recognize that proteins can be synthesized by different methods, for example, chemical methods or recombinant methods, as described in U.S. Pat. No. 4,617,149, which hereby is incorporated by reference.

The principles of solid phase chemical synthesis of polypeptides are well known in the art and may be found in general texts relating to this area. See, e.g., H. Dugas and C. Penney, *Bioorganic Chemistry* (1981) Springer-Verlag, New York, 54–92. Peptides may be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

The proteins of the present invention can also be made by recombinant DNA methods. Recombinant methods are preferred if a high yield is desired. Recombinant methods involve expressing the cloned gene in a suitable host cell. The gene is introduced into the host cell by any suitable means, well known to those skilled in the art. While chromosomal integration of the cloned gene is within the scope of the present invention, it is preferred that the cloned gene be maintained extra-chromosomally, as part of a vector in which the gene is in operable-linkage to a promoter.

Recombinant methods can also be used to overproduce a membrane-bound or membrane-associated protein. In some cases, membranes prepared from recombinant cells expressing such proteins provide an enriched source of the protein.

Expressing Recombinant Proteins in Procaryotic and Eucaryotic Host Cells

Procaryotes are generally used for cloning DNA sequences and for constructing vectors. For example, the Escherichia coli K12 strain 294 (ATCC No. 31446) is particularly useful for expression of foreign proteins. Other strains of E. coli, bacilli such as Bacillus subtilis, enterobacteriaceae such as Salmonella typhimurium or Serratia marcescans, various Pseudomonas species may also be employed as host cells in cloning and expressing the recombinant proteins of this invention. Also contemplated are various strains of Streptococcus and Streptocmyces.

For effective recombinant protein production, a gene must be linked to a promoter sequence. Suitable bacterial promoters include β-lactamase [e.g. vector pGX2907, ATCC 39344, contains a replicon and β-lactamase gene], lactose systems [Chang et al., Nature (London), 275:615 (1978); Goeddel et al., Nature (London), 281:544 (1979)], alkaline phosphatase, and the tryptophan (trp) promoter system [vector pATH1 (ATCC 37695)] designed for the expression of a trpE fusion protein. Hybrid promoters such as the tac promoter (isolatable from plasmid pDR540, ATCC-37282) are also suitable. Promoters for use in bacterial systems also will contain a Shine-Dalgarno sequence, operably linked to the DNA encoding the desired polypeptides. These examples are illustrative rather than limiting.

A variety of mammalian cells and yeasts are also suitable hosts. The yeast Saccharomyces cerevisiae is commonly used. Other yeasts, such as Kluyveromyces lactis, are also suitable. For expression of recombinant genes in Saccharomyces, the plasmid YRp7 (ATCC-40053), for example, may be used. See, e.g., L. Stinchcomb, et al., Nature, 282:39 (1979); J. Kingsman et al., Gene, 7:141 (1979); S. Tschemper et al., Gene, 10:157 (1980). Plasmid YRp7 contains the TRP1 gene, a selectable marker for a trp1 mutant.

Purification of Recombinantly-Produced Protein

An expression vector carrying a nucleic acid or gene of the present invention is transformed or transfected into a suitable host cell using standard methods. Cells that contain the vector are propagated under conditions suitable for expression of a recombinant protein. For example, if the gene is under the control of an inducible promoter, then suitable growth conditions would incorporate the appropriate inducer. The recombinantly-produced protein may be purified from cellular extracts of transformed cells by any suitable means.

In a preferred process for protein purification a gene is modified at the 5' end, or at some other position, such that the encoded protein incorporates several histidine residues (viz. "histidine tag"). This "histidine tag" enables "immobilized metal ion affinity chromatography" (IMAC), a single-step protein purification method described in U.S. Pat. No. 4,569,794, which hereby is incorporated by reference. The IMAC method enables isolation of substantially pure protein starting from a crude cellular extract.

As skilled artisans will recognize, owing to the degeneracy of the code, the proteins of the invention can be encoded by a large genus of different nucleic acid sequences. This invention further comprises said genus.

The ribonucleic acid compounds of the invention may be prepared using the polynucleotide synthetic methods discussed supra, or they may be prepared enzymatically using RNA polymerase to transcribe a DNA template.

The most preferred systems for preparing the ribonucleic acids of the present invention employ the RNA polymerase from the bacteriophage T7 or the bacteriophage SP6. These RNA polymerases are highly specific, requiring the insertion of bacteriophage-specific sequences at the 5' end of a template. See, J. Sambrook, et al., supra, at 18.82–18.84.

A This invention also provides nucleic acids that are complementary to the sequences disclosed herein.

The present invention also provides probes and primers, useful for a variety of molecular biology techniques including, for example, hybridization screens of genomic or subgenomic libraries, or detection and quantification of mRNA species as a means to analyze gene expression. A nucleic acid compound is provided comprising any of the sequences disclosed herein, or a complementary sequence thereof, or a fragment thereof, which is at least base pairs in length, and which will hybridize selectively to Streptococcus pneumoniae DNA or mRNA. Preferably, the 15 or more base pair compound is DNA. A probe or primer length of at least 15 base pairs is dictated by theoretical and practical considerations. See e.g. B. Wallace and G. Miyada, "Oligonucleotide Probes for the Screening of Recombinant DNA Libraries," In Methods in Enzymology, Vol. 152, 432–442, Academic Press (1987).

The probes and primers of this invention can be prepared by methods well known to those skilled in the art (See e.g. Sambrook et al. supra). In a preferred embodiment the probes and primers are synthesized by the polymerase chain reaction (PCR).

The present invention also relates to recombinant DNA cloning vectors and expression vectors comprising the nucleic acids of the present invention. Preferred nucleic acid vectors are those that comprise DNA. The skilled artisan understands that choosing the most appropriate cloning vector or expression vector depends on the availability of restriction sites, the type of host cell into which the vector is to be transfected or transformed, the purpose of transfection or transformation (e.g., stable transformation as an extrachromosomal element, or integration into a host chromosome), the presence or absence of readily assayable or selectable markers (e.g., antibiotic resistance and metabolic markers of one type and another), and the number of gene copies desired in the host cell.

Suitable vectors comprise RNA viruses, DNA viruses, lytic bacteriophages, lysogenic bacteriophages, stable bacteriophages, plasmids, viroids, and the like. The most preferred vectors are plasmids.

Host cells harboring the nucleic acids disclosed herein are also provided by the present invention. A preferred host is E. coli transfected or transformed with a vector comprising a nucleic acid of the present invention.

The invention also provides a host cell capable of expressing a gene described herein, said method comprising transforming or otherwise introducing into a host cell a recombinant DNA vector comprising an isolated DNA sequence that encodes said gene. The preferred host cell is any strain of E. coli that can accommodate high level expression of an exogenously introduced gene. Transformed host cells are cultured under conditions well known to skilled artisans, such that said gene is expressed, thereby producing the encoded protein in the recombinant host cell.

To discover compounds having antibacterial activity, one can look for agents that inhibit cell growth and/or viability by, for example, inhibiting enzymes required for cell wall biosynthesis, and/or by identifying agents that interact with membrane proteins. A method for identifying such compounds comprises contacting a suitable protein or membrane preparation with a test compound and monitoring by any suitable means an interaction and/or inhibition of a protein of this invention.

For example, the instant invention provides a screen for compounds that interact with the proteins of the invention, said screen comprising:

a) preparing a protein, or membranes enriched in a protein;
b) exposing the protein or membranes to a test compound; and
c) detecting an interaction of a protein with said compound by any suitable means.

The screening method of this invention may be adapted to automated procedures such as a PANDEX® (Baxter-Dade Diagnostics) system, allowing for efficient high-volume screening of compounds.

In a typical screen, a protein is prepared as described herein, preferably using recombinant DNA technology. A test compound is introduced into a reaction vessel containing said protein. The reaction/interaction of said protein and said compound is monitored by any suitable means. In a preferred method, a radioactively-labeled or chemically-labeled compound or protein is used. A specific association between the test compound and protein is monitored by any suitable means.

In such a screening protocol HPLFP is prepared as described herein, preferably using recombinant DNA technology. A test compound is introduced into a reaction vessel containing the HPLFP protein or fragment thereof. Binding of HPLFP by a test compound is determined by any suitable means. For example, in one method radioactively-labeled or chemically-labeled test compound may be used. Binding of the protein by the compound is assessed, for example, by quantifying bound label versus unbound label using any suitable method. Binding of a test compound may also be carried out by a method disclosed in U.S. Pat. No. 5,585,277, which hereby is incorporated by reference. In this method, binding of a test compound to a protein is assessed by monitoring the ratio of folded protein to unfolded protein, for example by monitoring sensitivity of said protein to a protease, or amenability to binding of said protein by a specific antibody against the folded state of the protein.

The foregoing screening methods are useful for identifying a ligand of a HPLFP protein, perhaps as a lead to a pharmaceutical compound for modulating the state of differentiation of an appropriate tissue. A ligand that binds HPLFP, or related fragment thereof, is identified, for example, by combining a test ligand with HPLFP under conditions that cause the protein to exist in a ratio of folded to unfolded states. If the test ligand binds the folded state of the protein, the relative amount of folded protein will be higher than in the case of a test ligand that does not bind the protein. The ratio of protein in the folded versus unfolded state is easily determinable by, for example, susceptibility to digestion by a protease, or binding to a specific antibody, or binding to chaperonin protein, or binding to any suitable surface.

The following examples more fully describe the present invention. Those skilled in the art will recognize that the particular reagents, equipment, and procedures described are merely illustrative and are not intended to limit the present invention in any manner.

EXAMPLE 1

Production of a Vector for Expressing S. pneumoniae dnaG in a Host Cell

An expression vector suitable for expressing S. pneumoniae dnaG in a variety of procaryotic host cells, such as E. coli, is easily made. The vector contains an origin of replication (Ori), an ampicillin resistance gene (Amp) useful for selecting cells which have incorporated the vector following a tranformation procedure, and further comprises the T7 promoter and T7 terminator sequences in operable linkage to the dnaG coding region. Plasmid pET11A (obtained from Novogen, Madison, Wis.) is a suitable parent plasmid. pET11A is linearized by restriction with endonucleases NdeI and BamHI. Linearized pET11A is ligated to a DNA fragment bearing NdeI and BamHI sticky ends and comprising the coding region of the S. pneumoniae dnaG (SEQ ID NO:1). The coding region for dnaG is easily produced by PCR technology using suitably designed primers to the ends of the coding region specified in SEQ ID NO:1.

The dnaG encoding nucleic acid used in this construct is slightly modified at the 5' end (amino terminus of encoded protein) in order to simplify purification of the encoded protein product. For this purpose, an oligonucleotide encoding 8 histidine residues is inserted after the ATG start codon. Placement of the histidine residues at the amino terminus of the encoded protein serves to enable the IMAC one-step protein purification procedure.

EXAMPLE 2

Recombinant Expression and Purification of a Protein Encoded by S. pneumoniae dnaG An expression vector that carries dnaG from the S. pneumoniae genome as disclosed herein and which dnaG is operably-linked to an expression promoter is transformed into E. coli BL21 (DE3) (hsdS gal 1cIts857 ind1Sam7nin5lacUV5-T7gene 1) using standard methods (see Example 4). Transformants, selected for resistance to ampicillin, are chosen at random and tested for the presence of the vector by agarose gel electrophoresis using quick plasmid preparations. Colonies which contain the vector are grown in L broth and the protein product encoded by the vector-borne ORF is purified by immobilized metal ion affinity chromatography (IMAC), essentially as described in U.S. Pat. No. 4,569,794.

Briefly, the IMAC column is prepared as follows. A metal-free chelating resin (e.g. Sepharose 6B IDA, Pharmacia) is washed in distilled water to remove preservative substances and infused with a suitable metal ion [e.g. Ni(II), Co(II), or Cu(II)] by adding a 50 nM metal chloride or metal sulfate aqueous solution until about 75% of the interstitial spaces of the resin are saturated with colored metal ion. The column is then ready to receive a crude cellular extract containing the recombinant protein product.

After removing unbound proteins and other materials by washing the column with any suitable buffer, pH 7.5, the bound protein is eluted in any suitable buffer at pH 4.3, or preferably with an imidizole-containing buffer at pH 7.5.

We claim:

1. An isolated nucleic acid fragment encoding a protein having the amino acid sequence that is SEQ ID NO:2.

2. An isolated nucleic acid fragment, wherein said fragment has a sequence selected from the group consisting of:
   (a) SEQ ID NO:1;
   (b) SEQ ID NO:3;
   (c) a nucleic acid fragment that encodes the same protein as (a) or (b), but which is degenerate in accordance with the degeneracy of the genetic code; and
   (d) a nucleic acid fragment fully complementary to (a), (b), or (c).

3. The isolated nucleic acid fragment of claim 2, wherein the sequence of said fragment is selected from the group consisting of SEQ ID NO:1, a sequence fully complementary to SEQ ID NO:1, and a nucleic acid fragment that encodes the same genetic information as either of the foregoing, but which is degenerate in accordance with the degeneracy of the genetic code.

4. The isolated nucleic acid fragment of claim 2, wherein the sequence of said fragment is selected from the group consisting of SEQ ID NO:3, a sequence fully complementary to SEQ ID NO:3, and a nucleic acid fragment that encodes the same genetic information as either of the foregoing, but which is degenerate in accordance with the degeneracy of the genetic code.

5. A vector comprising an isolated nucleic acid fragment, wherein said fragment has a sequence selected from the group consisting of:
   (a) SEQ ID NO:1; and
   (b) a nucleic acid fragment that encodes the same protein as (a), but which is degenerate in accordance with the degeneracy of the genetic code.

6. The vector of claim 5, wherein said isolated nucleic acid fragment is SEQ ID NO:1, operably-linked to a promoter sequence.

7. A recombinant host cell containing said vector of claim 5.

8. A recombinant host cell containing said vector of claim 6.

9. A method for constructing said recombinant host cell for expressing the protein of SEQ ID NO:2, said method comprising introducing into said host cell by any suitable means said vector of claim 6.

10. A method for expressing the protein of SEQ ID NO:2 in said recombinant host cell of claim 8, said method comprising culturing said recombinant host cell under conditions suitable for gene expression.

11. The method of claim 10, further comprising recovering said protein.

12. An isolated nucleic acid fragment consisting essentially of a nucleotide sequence encoding a protein having the amino acid sequence that is SEQ ID NO:2.

13. An isolated nucleic acid fragment, wherein said fragment consists essentially of a sequence selected from the group consisting of:
    (a) SEQ ID NO:1;
    (b) SEQ ID NO:3;
    (c) a nucleic acid fragment that encodes the same protein as (a) or (b), but which is degenerate in accordance with the degeneracy of the genetic code; and
    (d) a nucleic acid fragment fully complementary to (a), (b), or (c).

14. An isolated nucleic acid fragment of claim 13, wherein the sequence of said fragment is selected from the group consisting of:
    (a) SEQ ID NO:1;
    (b) a nucleic acid fragment that encodes the same protein as (a), but which is degenerate in accordance with the degeneracy of the genetic code; and
    (c) a sequence fully complementary to (a) or (b).

15. An isolated nucleic acid fragment of claim 13, wherein the sequence of said fragment is selected from the group consisting of:
    (a) SEQ ID NO:3;
    (b) a nucleic acid fragment that encodes the same protein as (a), but which is degenerate in accordance with the degeneracy of the genetic code; and
    (c) a sequence fully complementary to (a) or (b).

16. A vector comprising an isolated nucleic acid fragment, wherein said fragment consists essentially of a sequence selected from the group consisting of:
    (a) SEQ ID NO:1; and
    (b) a nucleic acid fragment that encodes the same protein as (a), but which is degenerate in accordance with the degeneracy of the genetic code.

17. The vector of claim 16, wherein said isolated nucleic acid fragment is SEQ ID NO:1, operably-linked to a promoter sequence.

18. A recombinant host cell containing said vector of claim 16.

19. A recombinant host cell containing said vector of claim 17.

20. A method for constructing a recombinant host cell for expressing the protein of SEQ ID NO:2, comprising introducing into said host cell by any suitable means said vector of claim 17.

21. A method for expressing a protein having the sequence shown in SEQ ID NO:2 in said recombinant host cell of claim 19, comprising culturing said recombinant host cell under conditions suitable for gene expression.

22. The method of claim 21, further comprising recovering said protein.

* * * * *